US011116745B2

(12) United States Patent
Gerstenberger et al.

(10) Patent No.: US 11,116,745 B2
(45) Date of Patent: Sep. 14, 2021

(54) PREBIOTIC FORMULATION

(71) Applicant: Deep Cell Industries, Inc., Seattle, WA (US)

(72) Inventors: James Gerstenberger, Seattle, WA (US); Kelly Ogilvie, Seattle, WA (US)

(73) Assignee: DEEP CELL INDUSTRIES, INC., Seattle, WA (US)

( * ) Notice: Subject to any disclaimer, the term of this patent is extended or adjusted under 35 U.S.C. 154(b) by 427 days.

(21) Appl. No.: 15/929,099

(22) Filed: Jan. 31, 2019

(65) Prior Publication Data

US 2019/0231736 A1    Aug. 1, 2019

Related U.S. Application Data

(60) Provisional application No. 62/624,611, filed on Jan. 31, 2018.

(51) Int. Cl.
*A61K 31/352* (2006.01)
*A61K 9/16* (2006.01)
(Continued)

(52) U.S. Cl.
CPC ............ *A61K 31/352* (2013.01); *A61K 9/146* (2013.01); *A61K 9/1652* (2013.01);
(Continued)

(58) Field of Classification Search
CPC .... A61K 31/352; A61K 9/146; A61K 9/1652; B01D 9/0009; B01D 21/009; C07C 37/004; C07C 51/43
See application file for complete search history.

(56) References Cited

U.S. PATENT DOCUMENTS 6,841,169 B2 * 1/2005 Hinrichs ............. C08B 37/0054
424/401
8,492,124 B2 * 7/2013 Ritter ........................ A61P 3/00
435/101
(Continued)

OTHER PUBLICATIONS

Acharya, N.; et al., "Endocannabinoid system acts as a regulator of immune homeostasis in the gut," PNAS. vol. 114, Issue 19, May 9, 2017, pp. 5005-5010.

(Continued)

*Primary Examiner* — Yate' K Cutliff
(74) *Attorney, Agent, or Firm* — Leber IP Law; Narendra K. Vaish; Shelly M. Fujikawa

(57) ABSTRACT

A method of generating an oligosaccharide encapsulated cannabidiol (CBD) formulation includes forming a cannabidiol ethanol mixture comprising ethanol and cannabidiol, forming an oligosaccharide CBD slurry by mixing the oligosaccharide with the cannabidiol ethanol mixture. The slurry is heated and mixed in a pressurized chamber to form a colloidal mixture, which is distributed into a tray as a layer. A cover is added to the tray to form an evaporation vessel, which is heated in a heating chamber. A rapid cooling process is performed on the colloidal mixture layer by removing the cover and spraying pulverized dry ice on the layer. The rapid cooling process is repeated until crystal formation is detected within the layer, the crystals including oligosaccharide encapsulated cannabidiol. An oligosaccharide encapsulated cannabidiol formulation includes cannabidiol and at least one oligosaccharide in a ratio in the range between about 1000:1 to 2200:1 (w/w) of CBD.

18 Claims, 5 Drawing Sheets

(51) Int. Cl.
  *B01D 9/00* (2006.01)
  *C07C 51/43* (2006.01)
  *B01D 21/00* (2006.01)
  *B01D 11/02* (2006.01)
  *A61K 9/14* (2006.01)
  *C07C 37/00* (2006.01)

(52) U.S. Cl.
  CPC ......... *B01D 9/0009* (2013.01); *B01D 9/0059* (2013.01); *B01D 11/0288* (2013.01); *B01D 11/0292* (2013.01); *B01D 21/009* (2013.01); *C07C 37/004* (2013.01); *C07C 51/43* (2013.01); *B01D 9/0036* (2013.01); *B01D 11/0203* (2013.01); *B01D 11/028* (2013.01)

(56) References Cited

U.S. PATENT DOCUMENTS

| | | | | |
|---|---|---|---|---|
| 9,815,810 | B1* | 11/2017 | Ogilvie | B01D 9/0009 |
| 2003/0229027 | A1* | 12/2003 | Eissens | A61K 9/1652 514/23 |
| 2011/0217426 | A1* | 9/2011 | Perry | A23L 33/10 426/103 |
| 2019/0183849 | A1* | 6/2019 | Kariman | A61K 31/352 |

OTHER PUBLICATIONS

Saulnier, D.M.; et al., "The intestinal microbiome, probiotics and probiotics in neurogastroenterology," Gut Microbes, Landes Bioscience, vol. 4, Issue 1, Jan./Feb. 2013, pp. 17-27.

Dipatrizio, N. V., "Endocannabinoids in the Gut," Cannabis and Cannabinoid Research, vol. 1, Issue 1, Feb. 24, 2016, pp. 67-77.

Slavin, J., "Fiber and Probiotics: Mechanisms and Health Benefits," Nutrients, vol. 5, Apr. 22, 2013, pp. 1417-1435.

Shoaib, M.; et al., "Inulin: Properties, health benefits and food applications," Carbohydrate Polymers, Elsevier, vol. 147, Aug. 20, 2016, pp. 444-454.

* cited by examiner

PREBIOTIC FORMULATION

CROSS-REFERENCE TO RELATED APPLICATIONS

This application claims the benefit of U.S. Provisional application Ser. No. 62/624,611, filed on Jan. 31, 2018, the entire contents of which are incorporated herein by reference in their entirety.

BACKGROUND

Human gut microflora play a key role in the intestinal immune system, in maintaining a disease-free state. The gut and immune system form a complex structure that provides defense against ingested toxins and pathogenic bacteria. A well-balanced gut microflora is thought to play a particularly important role in the natural defense of the human body. Gut microflora are found in the intestinal epithelium and the intestinal mucosal barrier that it secretes and have co-developed in a way that is tolerant to, and even supportive of, the gut flora that serves a barrier to pathogenic organisms. Some individuals may have gastrointestinal conditions that may be caused by, or exacerbated by, the lack of a healthy microbiota in their gut. These conditions (e.g., irritable bowel syndrome, Crohns disease, celiac disease, etc.) may present themselves with a variety of symptoms that includes intestinal inflammation that may inhibit the maintenance of a healthy microbiota.

Oligosaccharides may have many functions including cell recognition and cell binding. They are normally present as glycans: oligosaccharide chains linked to lipids or to compatible amino acid side chains in proteins, by N- or O-glygosidic bonds. N-linked oligosaccharides are always pentasaccharides attached to asparagine via a beta linkage to the amine nitrogen of the side chain. Alternately, O-linked oligosaccharides are generally attached to threonine or serine on the alcohol group of the side chain. Not all natural oligosaccharides occur as components of glycoproteins or glycolipids. Some, such as the raffinose series, occur as storage or transport carbohydrates in plants. Others, such as maltodextrins or cellodextrins, result from the microbial breakdown of larger polysaccharides such as starch or cellulose.

Referencing FIG. 1, a two dimensional skeletal structure is shown of a fructooligosaccharide 100 molecule. Fructooligosaccharides (FOS) are oligosaccharides that occur naturally in plants such as onion, chicory, garlic, asparagus, banana, artichoke, among many others. They are composed of linear chains of fructose units, linked by beta (2-1) bonds. The number of fructose units ranges from 2 to 60 and the units often terminate in a glucose unit. Dietary FOS are not hydrolyzed by small intestinal glycosidases and reach the cecum structurally unchanged. There, they are metabolized by the intestinal microflora to form short-chain carboxylic acids, L-lactate, CO(2), hydrogen and other metabolites. FOS have a number of interesting properties, including a low sweetness intensity; they are also calorie free, non-cariogenic and are considered as soluble dietary fibre. Furthermore, FOS have important beneficial physiological effects such as low carcinogenicity, a prebiotic effect, improved mineral absorption and decreased levels of serum cholesterol, triacylglycerols and phospholipids.

Because of the configuration of their glycosidic bonds, fructooligosaccharides resist hydrolysis by salivary and intestinal digestive enzymes. In the colon they are fermented by anaerobic bacteria. In other words, they have a lower caloric value, while contributing to the dietary fiber fraction of the diet. Fructooligosaccharides are more soluble than inulins and are, therefore, sometimes used as an additive to yogurt and other (dairy) products. Fructooligosaccharides are used specially in combination with high-intensity artificial sweeteners, whose sweetness profile and aftertaste they improve.

Currently, FOS are included in food products and infant formulas due to their prebiotic effect to stimulate the growth of nonpathogenic intestinal microflora. Their consumption increases fecal bolus and the frequency of depositions, while a dose of 4-15 g/day given to healthy subjects will reduce constipation, considered one of the growing problems of modern society and newborns during the first months of life.

Referencing FIG. 2, a two dimensional skeletal structure of a galactooligosaccharide 200 molecule is shown. Galactooligosaccharides (GOS), which also occur naturally, consist of short chains of galactose molecules. GOS generally comprise a chain of galactose units that arise through consecutive transgalactosylation reactions, with a terminal glucose unit. However, where a terminal galactose unit is indicated, hydrolysis of GOS formed at an earlier stage in the process has occurred. The degree of polymerization of GOS can vary quite markedly, ranging from 2 to 8 monomeric units, depending mainly on the type of the enzyme used and the conversion degree of lactose.

GOS, is also known as oligogalactosyllactose, oligogalactose, oligolactose or transgalactooligosaccharides (TOS) and may be utilized as a prebiotic. Prebiotics are defined as non-digestible food ingredients that beneficially affect the host by stimulating the growth and/or activity of beneficial bacteria in the colon. These compounds cannot be digested in the human small intestine, and instead pass through to the large intestine, where they promote the growth of Bifidobacteria, which are beneficial to gut health.

While prebiotics are available to help promote growth of beneficial gut bacteria, they may not stop inflammatory responses in the epithelial cells that expel the mucosa lining containing them.

Referencing FIG. 3, a two dimensional skeletal structure of a cannabidiol 300 molecule is shown. Cannabidiol (CBD) is a degradative product of Cannabidiolic acid due to decarboxylation following exposure to heat and/or air. CBD is a major phytocannabinoid, accounting for up to 40% of cannabis plant's extract. Cannabidiol has been shown to have many therapeutic pharmacological effects. Cannabidiol has shown very low affinity for the cannabinoid $CB_1$ and $CB_2$ receptors but acts as an indirect antagonist of these receptors. Similar to THC, CBD has been shown to inhibit gastrointestinal activity after administration. This effect is assumed to be a $CB_1$-mediated response, since this receptor is expressed by the peptide hormone cholecystokinin, and application of the $CB_1$-specific inverse agonist SR 141716A (Rimonabant) blocks the effect.

In some studies, CBD has shown the ability to reduce and prevent gut inflammation from the activation of enteric glial cells (EGC). Enteric glial cells maintain the integrity of gut mucosa and act as immuno-competent cells against pathogenic stimuli. Enteric glial cells actively mediate acute and chronic inflammation in the gut by releasing neurotrophins, growth factors, and pro-inflammatory cytokines, which amplify an immune response to defend against pathogens. In some individuals, this immune response may be activated due to abnormalities in the regulation of enteric glial cells, resulting in chronic intestinal inflammation. These abnormalities may be linked to Crohn's disease or ulcerative colitis. In these individuals, reactive enteric glial cells exhibit an over-expression and secretion of S100B protein, a cell-specific astroglial derived signaling molecule that results in chronic intestinal inflammation leading to intestinal damage and disruption of gut microbiota. CBD was shown to reduce the expression of S100B and iNOS proteins, counteracting enteric reactive gliosis caused by over active Enteric glial cells. Additionally, pre-treatment with CBD was able to prevent glial cell hyper-activation in the intestine.

However, the solubility of cannabidiol is low resulting in a low oral bioavailability (i.e., 13-19% absorption). This low bioavailability and solubility limits the use of cannabidol in some prebiotic formulations.

Therefore, a need exists for a formulation that promotes gut microflora and reduces intestinal inflammation.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
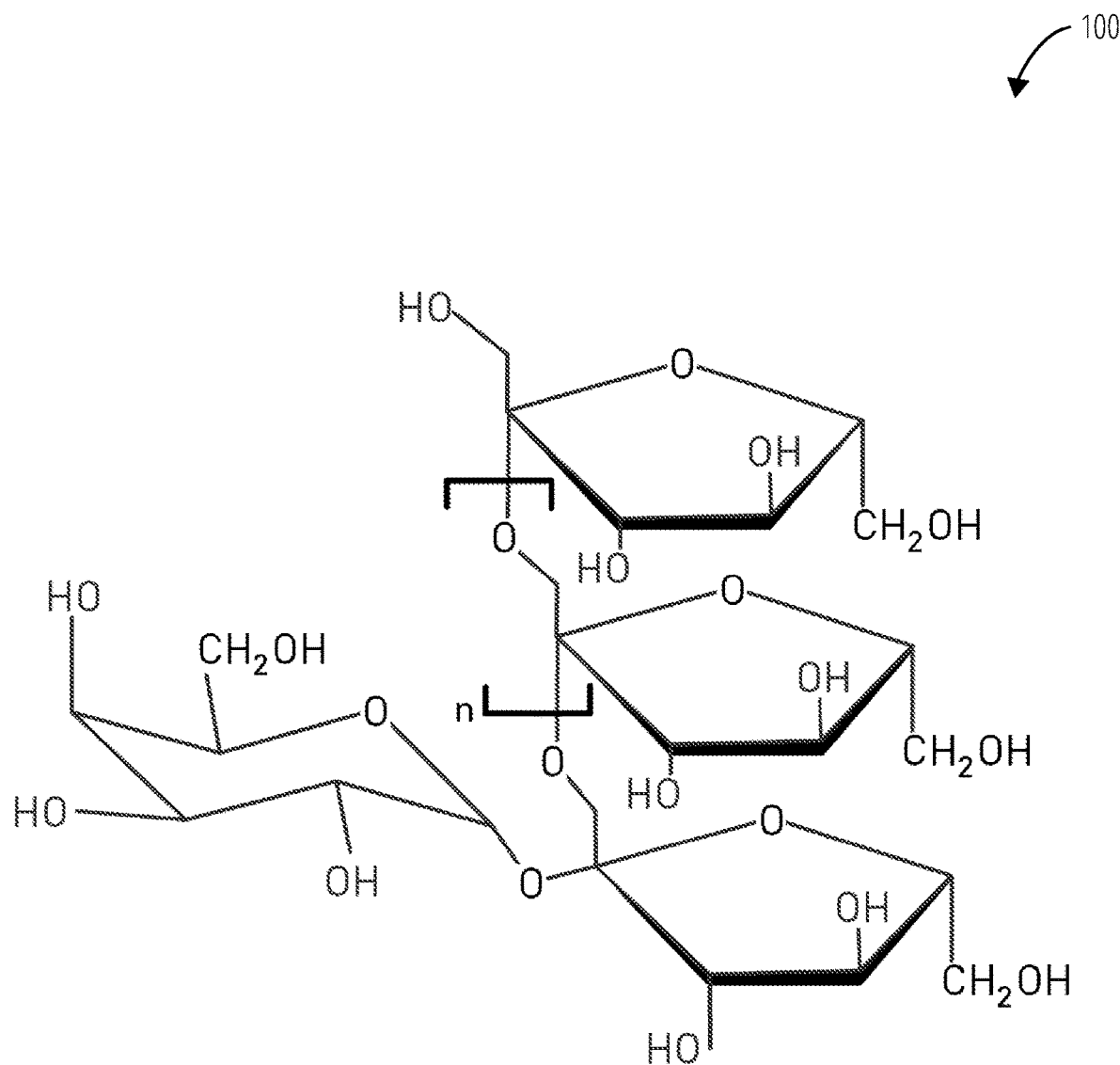
FIG. 1 illustrates a fructooligosaccharide 100 in accordance with one embodiment.
Figure 2:
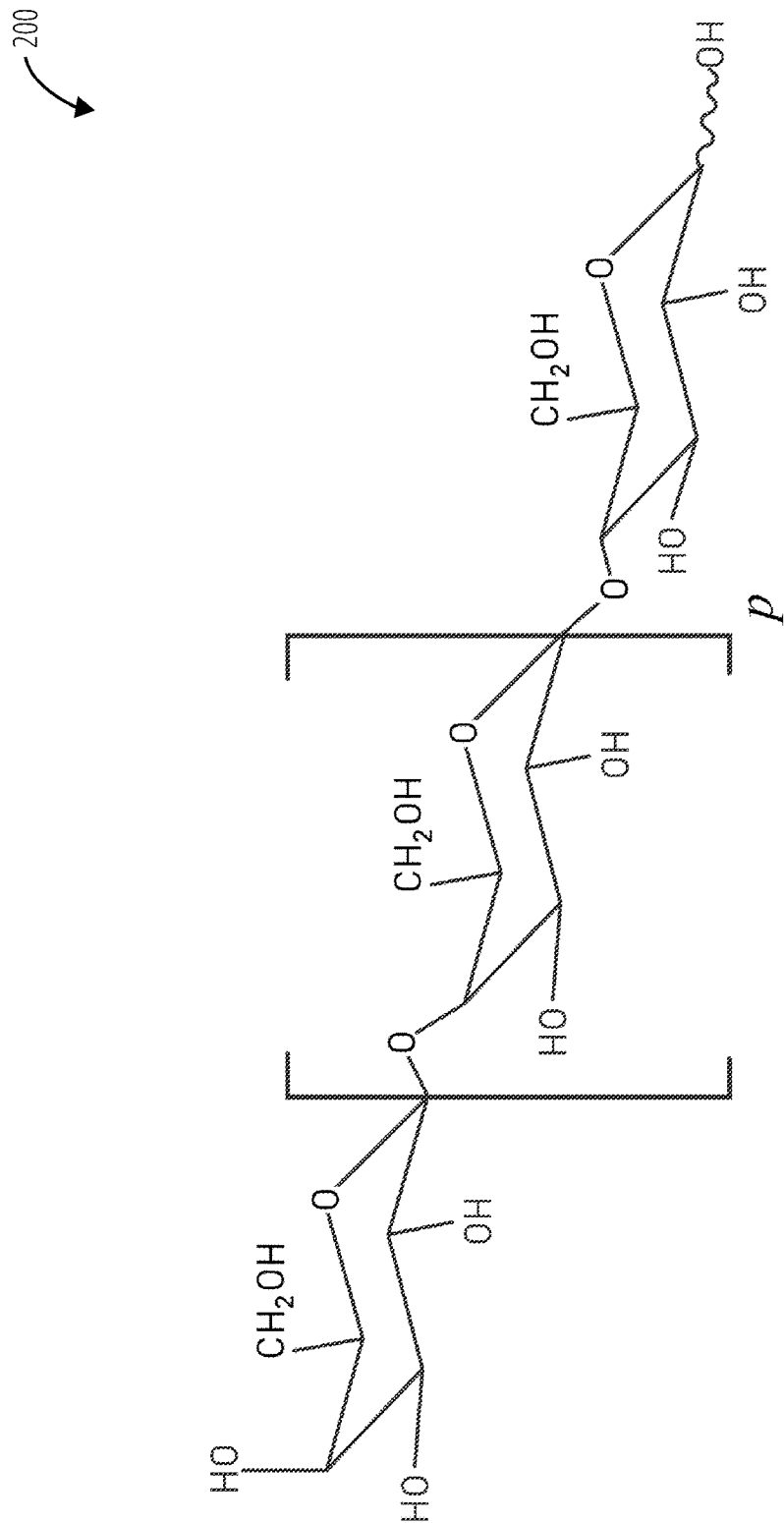
FIG. 2 illustrates a galactooligosaccharide 200 in accordance with one embodiment.
Figure 3:
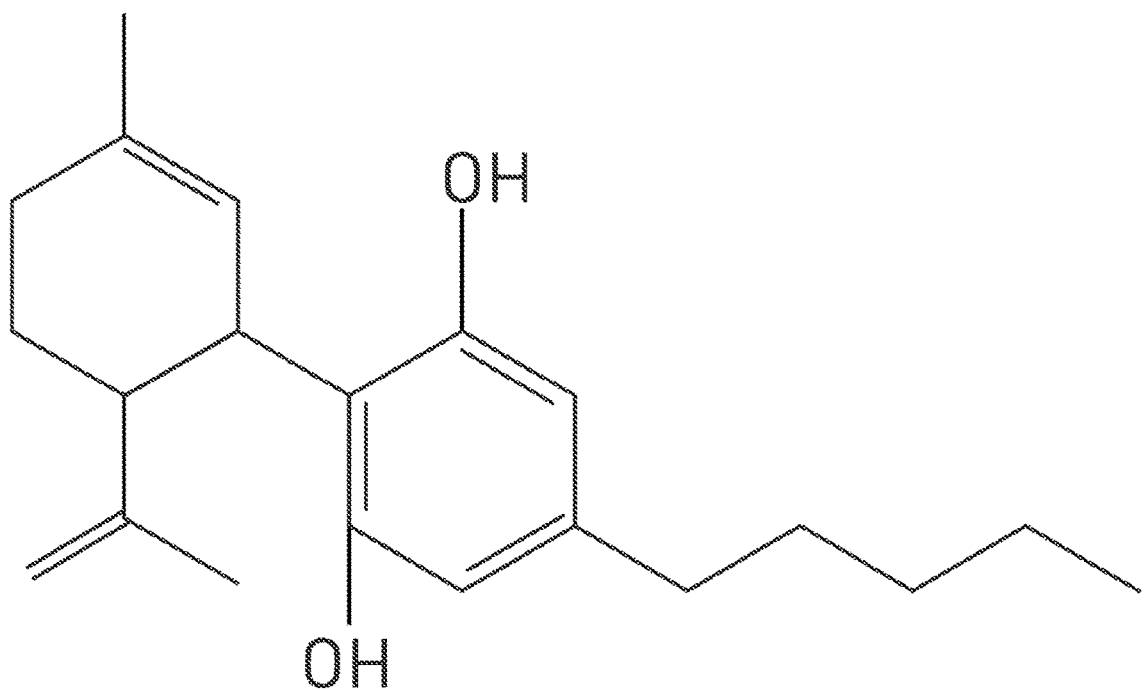
FIG. 3 illustrates a cannabidiol 300 in accordance with one embodiment.

A method of generating an oligosaccharide encapsulated cannabidiol formulation involves forming a cannabidiol ethanol mixture comprising ethanol and cannabidiol ranging between about 0.05 to 2.5 w % of the cannabidiol ethanol mixture in a first reactor. The method then forms an oligosaccharide CBD slurry by mixing at least one oligosaccharide with the cannabidiol ethanol mixture, in a ratio ranging between 1:6 to 5:3 by weight of the cannabidiol ethanol mixture in a second reactor. The method then heats and mixes the oligosaccharide cannabidiol slurry at temperature ranging between 175° F. to 225° F. in a pressurized chamber between 45 and 75 minutes to form a colloidal mixture. The colloidal mixture is then distributed into a tray forming an evenly distributed mixture layer with a depth ranging between 2.0" and 4.0" inches. Once the tray has been loaded an evaporation vessel is formed through the attachment of a detachable cover to the tray enclosing the evenly distributed mixture layer. The method then positions and heats the evaporation vessel within a heating chamber to a temperature ranging between 225° F. and 300° F. As the evenly distributed mixture layer approaches a saturation temperature a rapid cooling process performed. The rapid cooling process involves temporarily removing the detachable cover from the tray to expose the evenly distributed mixture layer within the evaporation vessel. Afterwards, pulverized dry ice is sprayed on the evenly distributed mixture layer. After which, the detachable cover is reattached to the tray forming the evaporation vessel. The method may repeat the rapid cooling process until crystal formation is detected within the evenly distributed mixture layer. Once the crystal formation is detected, the evaporation vessel is removed from the heating chamber. The crystal formation comprises the oligosaccharide encapsulated cannabidiol as a crystalline product.

In some configurations, the oligosaccharide encapsulated cannabidiol comprises the at least one oligosaccharide in a ratio in the range between about 1000:1 to 2200:1 (w/w) of CBD. In another configuration, the oligosaccharide encapsulated cannabidiol comprises the at least one oligosaccharide in a ratio in the range between about 1800:1 to 2200:1 (w/w) of CBD. In another configuration, the oligosaccharide encapsulated cannabidiol comprises the at least one oligosaccharide in a ratio in the range between about 2000:1 to 2200:1 (w/w) of CBD. In another configuration, the at least one oligosaccharide is found in a ratio of about 2000:1 (w/w) of CBD. In another configuration, the at least one oligosaccharide is found in a ratio of about 1000:1 (w/w) of CBD. In another configuration, the at least one oligosaccharide is found in a ratio of about 500:1 (w/w) of CBD.

In some configurations, the at least one oligosaccharide comprises at least a fructooligosaccharide, a galactooligosaccharide, and combinations thereof.

An oligosaccharide encapsulated cannabidiol formulation for improving the health of human gut microbiota includes cannabidiol (CBD) and at least one oligosaccharide. The at least one oligosaccharide may be found in a ratio in the range between about 1000:1 to 2200:1 (w/w) of CBD. The at least one oligosaccharide may be found in a ratio in the range between about 1800:1 to 2200:1 (w/w) of CBD. The at least one oligosaccharide may be found in a ratio in the range between about 2000:1 to 2200:1 (w/w) of CBD. The at least one oligosaccharide of the oligosaccharide encapsulated cannabidiol formulation may comprise fructooligosaccharide. The at least one oligosaccharide of the oligosaccharide encapsulated cannabidiol formulation may comprise galactooligosaccharide. In one configuration, the at least one oligosaccharide in the oligosaccharide encapsulated cannabidiol formulation is found in a ratio of about 2000:1 (w/w) of CBD. In another configuration, the at least one oligosaccharide is found in a ratio of about 2000:1 (w/w) of CBD. In yet another configuration, the at least one oligosaccharide is found in a ratio of about 1000:1 (w/w) of CBD. In another configuration, the at least one oligosaccharide is found in a ratio of about 500:1 (w/w) of CBD.

In some configurations, the oligosaccharide encapsulated cannabidiol formulation may incorporate a phytocanabinoid and/or synthetic/semisynthetic phytocannabinoid instead of or in addition to cannabidiol. In configurations of the oligosaccharide encapsulated cannabidiol formulation where cannabidiol is substituted by the phytocanabinoid and/or synthetic/semisynthetic phytocannabinoid, the phytocanabinoid and/or synthetic/semisynthetic phytocannabinoid may be found in ratios similar to the cannabidiol. In configurations of the oligosaccharide encapsulated cannabidiol formulation where the phytocanabinoid and/or synthetic/semisynthetic phytocannabinoid are found in addition to the cannabidiol, the combined ratio of the phytocanabinoid and/or synthetic/semisynthetic phytocannabinoid and cannabidiol may be the same as in the configuration of the oligosaccharide encapsulated cannabidiol formulation with just cannabidiol. Alternatively, the phytocanabinoid and/or synthetic/semisynthetic phytocannabinoid may be found in ratios related to either cannabidiol or the at least one oligosaccharide, independent of the existing ratio between the in the oligosaccharide encapsulated cannabidiol formulation Although cannabidiol and oligosaccharides can be found in certain plants, their concentrations never approach a ratio of about 1:2000 (CBD to at least one oligosaccharide). Furthermore, naturally occurring instances of cannabidiol and an at least one oligosaccharide contain measurable quantities of Δ-9-tetrahydrocannabinol (Δ9-THC). Moreover, naturally occurring instances of cannabidiol and oligosaccharides lack homogeneity resulting in consistent ratios depending on where a sample is taken.

The creation of the oligosaccharide encapsulated cannabidiol formulation may involve an ethanol extraction of CBD from plant material with negligible or no amount Δ9-THC present. The extracted CBD in the ethanol is filtered and heated to remove any Δ9-THC still present. A purified form of at least one oligosaccharide is added to filtered ethanol CBD wash while it is stirred and heated for a predetermined amount of time. Due to the high quantities of the at least one oligosaccharide utilized in the oligosaccharide encapsulated cannabidiol formulation, the ethanol mixture becomes saturated. The saturated mixture is then cooled, allowing formation of a precipitate that is then dried further until any remaining ethanol has evaporated. The resulting crystalline product contains the cannabidiol and the at least one oligosaccharide in the expected ratio.

Furthermore, the about 2000:1 (w/w) of the at least one oligosaccharide and CBD limits bactericidal effects of CBD while specifically promoting anti-inflammatory responses in the gut.

Figure 4:
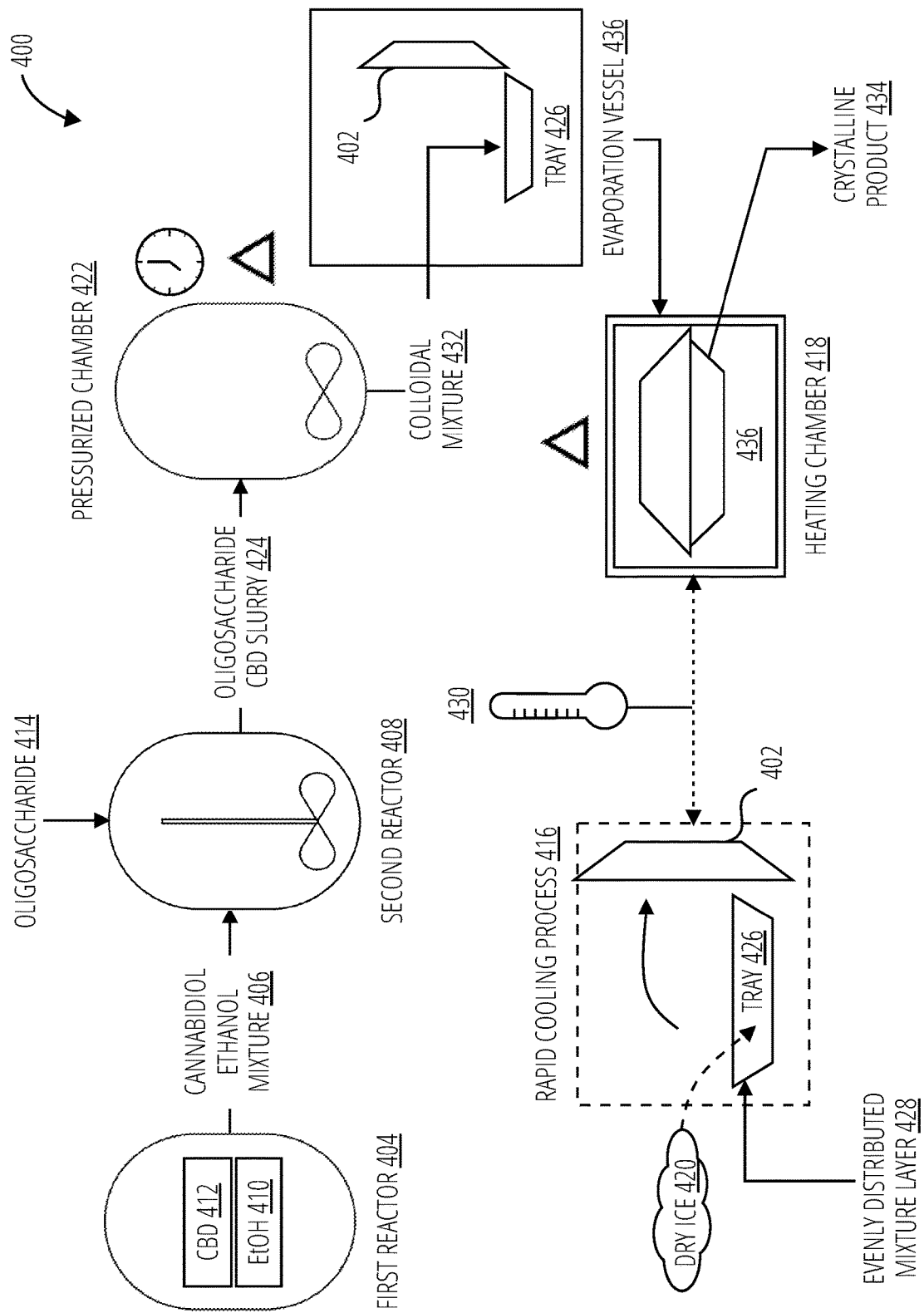
FIG. 4 illustrates a system 400 generating an oligosaccharide encapsulated cannabidiol formulation in accordance with one embodiment.

Referring to FIG. 4, a system 400 generating an oligosaccharide encapsulated cannabidiol formulation comprises a first reactor 404, a second reactor 408, a pressurized chamber 422, an evaporation vessel 436, and a heating chamber 418. The first reactor 404 combines cannabidiol 412 and ethanol 410 to form a cannabidiol ethanol mixture 406. The cannabidiol ethanol mixture 406 may then be transferred into second reactor 408 where it is mixed with an at least one oligosaccharide 414 to form an oligosaccharide CBD slurry 424. The at least one oligosaccharide 414 may be provided as a solid in powdered form when added to the second reactor 408. The oligosaccharide CBD slurry 424 may then be transferred to a pressurized chamber 422 where it is heated and mixed/agitated at a temperature ranging between about 175° F. to 225° F. between about 45 and 75 minutes in order to form a colloidal mixture 432. The colloidal mixture 432 is then distributed onto the tray 426 with a depth ranging between about 2.0 inches and 4.0 inches forming an evenly distributed mixture layer 428. A detachable cover 402 is then placed on top of the tray forming an evaporation vessel 436. The evaporation vessel 436 is then placed within the heating chamber 418 in a temperature ranging between about 225° F. and 300° F. A rapid cooling process 416 is performed when the evenly distributed mixture layer 428 approaches its saturation temperature 430. During the rapid cooling process 416, the detachable cover 402 is temporarily removed from the tray exposing the evenly distributed mixture layer 428 within the evaporation vessel 436. Pulverized dry ice 420 is then sprayed on the evenly distributed mixture layer 428, and the detachable cover 402 is repositioned on top of the tray 426 enclosing the evenly distributed mixture layer 428 in the evaporation vessel 436. The rapid cooling process 416 is repeated until crystal formation is detected within the evenly distributed mixture layer 428 indicating the formation of the crystalline product 434.

Figure 5:
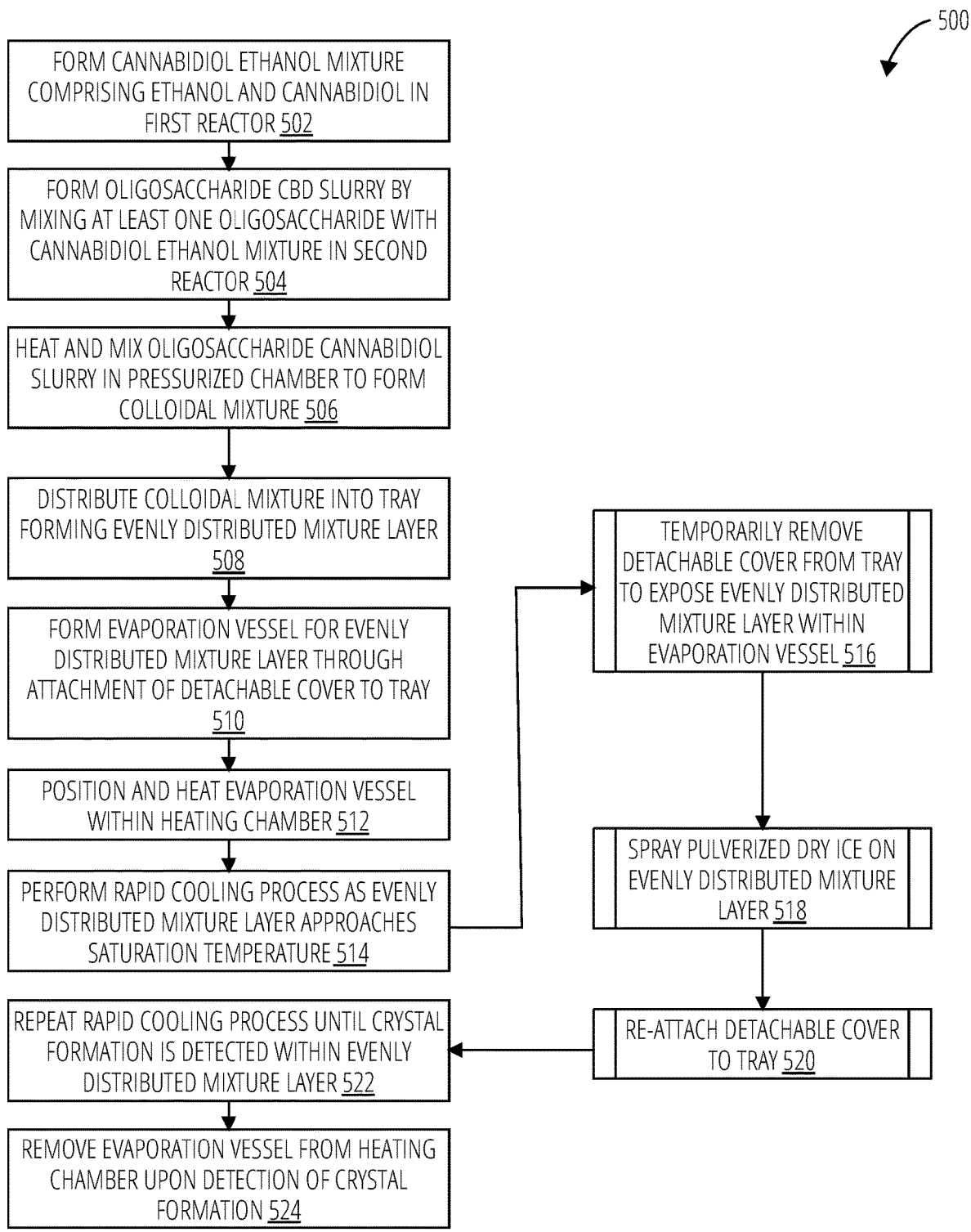
FIG. 5 illustrates a manufacturing method 500 in accordance with one embodiment.

The system 400 may be operated in accordance with the process described in FIG. 5.

Referencing FIG. 5, a method 500 of generating an oligosaccharide encapsulated cannabidiol formulation involves forming a cannabidiol ethanol mixture comprising ethanol and cannabidiol rings between about 0.05 to 2.5 w % of the cannabidiol ethanol mixture in a first reactor (block 502). In block 504, the method 500 forms an oligosaccharide CBD slurry by mixing at least one oligosaccharide with the cannabidiol ethanol mixture, in a ratio ranging between about 1:6 to 5:3 by weight of the cannabidiol ethanol mixture in a second reactor. In block 506, the method 500 heats and mixes the oligosaccharide cannabidiol slurry at temperature ranging between about 175° F. to 225° F. in a pressurized chamber between about 45 and 75 minutes to form a colloidal mixture. In block 508, the method 500 distributes the colloidal mixture into a tray forming an evenly distributed mixture layer with a depth ranging between 2.0 inches and 4.0 inches. In block 510, the method 500 forms an evaporation vessel for the evenly distributed mixture layer through the attachment of a detachable cover to the tray. In block 512, the method 500 positions and heats the evaporation vessel within a heating chamber to a temperature ranging between about 225° F. and 300° F. In block 514, the method 500 performs a rapid cooling process as the evenly distributed mixture layer approaches a saturation temperature. In subroutine block 516, the rapid cooling process temporarily removes the detachable cover from the tray to expose the evenly distributed mixture layer within the evaporation vessel. In subroutine block 518, the rapid cooling process sprays pulverized dry ice on the evenly distributed mixture layer. In subroutine block 520, the rapid cooling process re-attaches the detachable cover to the tray. In block 522, the method 500 repeats the rapid cooling process until crystal formation is detected within the evenly distributed mixture layer. In block 524, the method 500 removes the evaporation vessel from the heating chamber upon detection of crystal formation, wherein the crystal formations comprise oligosaccharide encapsulated cannabidiol as a crystalline product.

The disclosed processes for cannabidiol encapsulation in oligosaccharides may be utilized to infuse oligosaccharide lattice structures with cannabidiol. The cannabidiol may be phytocannabinoid derived from a Cannabis sativa L. variety but may be any phytocanabinoid and/or synthetic/semisynthetic phytocannabinoid instead of or in addition to cannabidiol. The processes may be utilized to infuse cannabidiol in crystallized oligosaccharides such as a fructo-oligosaccharide, galacto-oligosaccharide, etc. The crystalline products formed thereby may reduce the degradation of cannabidiol during long-term storage and increase bioavailability.

The disclosed processes may be utilized to stabilize, fuse, and encapsulate cannabidiol using oligosaccharides through the utilization of heat, pressure, and rapid temperature oscillation to facilitate and induce crystallization for the encapsulation process.

One embodiment may include the use of cannabis extracts from a supercritical and subcritical carbon dioxide extraction, hydrocarbon extraction, or water extraction in combination with the alcohol extraction and a membrane filtration process to separate a cannabinoid ethanol mixture. The processes may utilize glucose, fructose, sucrose, sodium chloride, and xylitol as the crystalline compound to create a crystalline structure in combination with the use of alcohol and membrane filters. The filtration process may combine cannabinoid extract with an alcohol at about 200° Fahrenheit (93° Celsius), to aid in dissolution, followed by vigorous agitation.

An oligosaccharide cannabidiol slurry may be formed by blending and agitating the ethanol cannabinoid mixture with the at least one oligosaccharide by placing the oligosaccharide cannabidiol slurry into a pressure chamber and heating the slurry to about 200° Fahrenheit (93° Celsius) for sixty minutes. An additional oligosaccharide may be added to the oligosaccharide cannabidiol slurry to seed crystal formation and the mixture may be heated to about 220° Fahrenheit (104° Celsius) for another sixty minutes. The crystal size of the product may be homogenized during a polishing step.

The crystalline product may be a nearly pure cannabinoid infused crystal, which may be a sugar, salt or sugar-alcohol crystal that is useful for preserving cannabinoids against degradation in a biologically available and ecologically safe crystalline formulation. The preservation process may preserve phytocannabinoid compounds by fusing the extracted phytocannabinoid compounds into oligosaccharide crystals. The lattice structure and optical characteristics of the infused crystal assist in the preservation and stability of the phytocannabinoid compound for long-term storage and use in medicaments.

The term fusing refers to the process of suspending phytocannabinoid compounds in crystalline compounds structures by using the methods disclosed. The method of cannabinoid encapsulation may prevent the phytocannabinoid compounds from being damaged by exposure to light, oxygen, chlorophylls, and free radicals, all of which are known to degrade cannabinoids.

The crystal bond orientation prevents chemical, photo-oxidation and further decarboxylation of the cannabidiol as well as other phytocanabinoids and/or synthetic/semisynthetic phytocannabinoids. The method of cannabinoid preservation is suitable for other forms of molecular stabilization. The method utilizes membrane filtration to aid in stability and solubility, as well as the use of temperature oscillation to change the chemical nature of the crystalline product.

In some embodiments, cannabidiol fused into the crystal lattices of a combination of oligosaccharides that may include fructoolisaccharide and galactooligosaccharide and combinations thereof. In some embodiments, the lattice structure of the crystalline form of fructoolisaccharide and galactooligosaccharide may be manipulated through external forces, (e.g., pressure, temperature, chemical, etc.) to modify the lattice structure and formation.

Principles of green chemistry may be implemented to provide safe alternatives to industrial pharmaceutical manufacturing processes. The oligosaccharide encapsulated cannabidiol crystalline product may experience improved uptake and absorption as well as sustained bioavailability imparted by the digestion and absorption patterns associated with consumption of unaltered oligosaccharides. In addition, the oligosaccharide encapsulated cannabidiol within the crystalline product may be well suited for use in edible medicaments as a result of the hydrolysis of the disaccharides into fructose and glucose. The process may improve the absorption of cannabidiol during digestion, without decreased bioavailability from excessive absorption into the stomach and liver tissues. The process may provide improved water solubility, which aids in its use as a medicament.

Investigation into the potency of cannabidiol in the crystalline product utilizing the encapsulation process found the potency to be about 1.83 mg/g on a first run and about 2.3 mg/g on a second run. Due to protection in parted by the encapsulation process, losses in potency may be minimal.

An oligosaccharide encapsulated cannabidiol crystallin product that results from the application of the disclosed encapsulation processes may prevent oxidation, decarboxylation, and degradation to the cannabidiol, which is bound to non-lipid molecules aiding use in preservation and consumption. The crystalline product of the encapsulation process exhibits unique chemical properties comprising resistance to heat, light, spoilage, and excessive metabolic absorption in the body when consumed.

The process may carry beneficial improvements in absorption rates, as cannabidiol requires a complex digestion pathway, whereas the crystalline product may adopt the digestion pathway and absorption profile of the oligosaccharide.

Ethanol is selected as the alcohol solvent due to its solvation properties and low toxicity to humans. The ratio of ethanol to cannabidiol extract may be about 4:1 to 8:1, but may be about 5:1, about 6:1, or about 7:1. A ratio between about 4:1 and 8:1 allows a full blending as well as control over the final concentration of the cannabidiol in the crystal matrix.

The method of cannabidiol encapsulation may utilize a mixer that has a mechanical agitation speed of at least about 20,000 rpm. Additional agitation speeds and ranges may be utilized to accommodate variations and improvements to the manufacturing process. The blended mixture of cannabinoids and alcohols may be above about 150° Fahrenheit (66° Celsius) for handling, mixing and homogenization.

The at least one oligosaccharide and cannabidiol ethanol mixture may be agitated and blended into an oligosaccharide cannabidiol slurry. The oligosaccharide cannabidiol slurry may be combined in a reactor comprising a mixer/agitator that has a minimum agitation speed of about 20,000 rpm. The oligosaccharide cannabidiol slurry may be agitated for a period of time that exceeds five minutes. The oligosaccharide cannabidiol slurry may be heated to about 200° Fahrenheit (93° Celsius) in a pressure chamber for about sixty minutes or a period of time adapted to accommodate improvements or modifications to the manufacturing process. The pressure chamber is heated to a temperature range of about 200° to 250° Fahrenheit (93 to 121° Celsius) at normal atmospheric pressure. At higher pressures ranging from about two atmospheres (202 kpa) the temperature range is between about 250° to 300° Fahrenheit (121 to 148° Celsius).

The oligosaccharide cannabidiol slurry may be transferred to a tray and spread evenly to form an evenly distributed layer. The evenly distributed layer material may be provided with a depth ranging between about 25-50% of the height of the tray. The depth of the distributed layer is dependent on exposed surface area of the evenly distributed layer to facilitate vaporization of excess ethanol. The tray is coupled to a detachable cover that partially seals the evenly distributed layer forming an evaporation vessel. The evaporation vessel serves as a partially sealed enclosure that impedes rapid vaporization of alcohol under heat while reducing factors that could lead to the auto ignition of the alcohol vapors.

The evaporation vessel may be placed within a heating chamber and monitored for the saturation temperature/boiling point of the evenly distributed layer. Upon detection that the evenly distributed layer is approaching the saturation temperature/boiling point, the detachable cover of the evaporation vessel is removed, and the evenly distributed layer is sprayed with pulverized dry ice as part of a rapid cooling process. The evenly distributed layer is inspected to determine nucleation or crystal growth before the detachable cover is reattached to the tray. During the rapid cooling process, the evaporation vessel remains within the heating chamber. The rapid cooling process is repeated until crystal growth is detected or all the ethanol has been boiled off.

The pulverized dry ice ($CO_2$) may be substituted with another super cooled substance that may include but is not limited to liquid nitrogen. Dry ice may be selected preferentially based on its sublimation properties. The sublimation of dry ice in an alcohol containing fluid increases vaporization by allowing the saturation pressure to be reached below the normal saturation temperature. Removal of alcohol through dry ice simultaneously lowers the temperature of the cannabinoids. The evaporation vessel may be removed from the heating chamber following detection of crystal growth in the evenly distributed layer following application of the rapid cooling process.

The encapsulation process may include a further step wherein micronized crystalline product is added to the colloidal mixture at the midway point of the process and at peak temperature. The micronized material may be a pulverized form of the crystalline product utilized to seed crystal formation as ethanol evaporates from the oligosaccharide cannabidiol slurry and the oligosaccharide cannabidiol crystals nucleate.

The encapsulation process may further include the addition of the crystalline product (i.e., cannabidiol encapsulated in the oligosaccharide) to the oligosaccharide cannabidiol slurry to seed the crystal formation.

A system for generating an oligosaccharide encapsulated cannabidiol formulation may include a first reactor, a filtration process, a second reactor, a pressurized chamber, an evaporation vessel, a heating chamber, a tray, and/or an evenly distributed mixture layer.

The evaporation vessel may include a detachable cover detachably coupled to a tray. The first reactor may be operatively disposed to receive cannabidiol and ethanol. The first reactor may be in fluid communication with the second reactor for delivery of a cannabidiol ethanol mixture. The second reactor may be operatively disposed to receive the at least one oligosaccharide, and the pressurized chamber may be operatively disposed to receive an oligosaccharide cannabidiol slurry from the second reactor.

In some embodiments, the tray may be operatively disposed to receive a colloidal mixture from the pressurized chamber forming an evenly distributed mixture layer. The evenly distributed mixture layer may be encloseably positioned within the evaporation vessel and the evaporation vessel may be positionable within the heating chamber. The evenly distributed mixture layer may be in fluid communication with pulverized dry ice following detachment of the detachable cover from the tray during the rapid cooling process.

The methods and systems in this disclosure are described in the preceding on the basis of several preferred embodiments. Different aspects of different variants are considered to be described in combination with each other such that all combinations that upon reading by a skilled person in the field on the basis of this document may be regarded as being read within the concept of the invention. The preferred embodiments do not limit the extent of protection of this document.

Having thus described embodiments of the present invention of the present application in detail and by reference to illustrative embodiments thereof, it will be apparent that modifications and variations are possible without departing from the scope of the present invention.

What is claimed is:

1. A method of generating an oligosaccharide encapsulated cannabidiol (CBD) formulation comprises:
    forming a cannabidiol ethanol mixture comprising ethanol and cannabidiol ranging between about 0.05 to 2.5 w % of the cannabidiol ethanol mixture in a first reactor;
    forming an oligosaccharide CBD slurry by mixing at least one oligosaccharide with the cannabidiol ethanol mixture, in a ratio ranging between about 1:6 to 5:3 by weight of the cannabidiol ethanol mixture in a second reactor;
    heating and mixing the oligosaccharide CBD slurry in a pressurized chamber to form a colloidal mixture;
    distributing the colloidal mixture into a tray forming a distributed mixture layer;
    forming an evaporation vessel for the distributed mixture layer through the attachment of a detachable cover to the tray;
    positioning the evaporation vessel within a heating chamber and heating the evaporation vessel within the heating chamber;
    performing a rapid cooling process as the distributed mixture layer approaches a saturation temperature by:
        temporarily removing the detachable cover from the tray to expose the distributed mixture layer within the evaporation vessel;
        spraying pulverized dry ice on the distributed mixture layer; and
        re-attaching the detachable cover to the tray;
    repeating the rapid cooling process until crystal formation is detected within the distributed mixture layer; and
    removing the evaporation vessel from the heating chamber upon detection of crystal formation, wherein the crystal formations comprises oligosaccharide encapsulated cannabidiol as a crystalline product and the oligosaccharide encapsulated cannabidiol comprises the at least one oligosaccharide in a ratio in the range between about 1000:1 to 2200:1 (w/w) of CBD.

2. The method of claim 1, wherein the oligosaccharide encapsulated cannabidiol comprises the at least one oligosaccharide in a ratio in the range between about 2000:1 to 2200:1 (w/w) of CBD.

3. The method of claim 1, wherein the oligosaccharide encapsulated cannabidiol comprises the at least one oligosaccharide in a ratio in the range between about 1800:1 to 2200:1 (w/w) of CBD.

4. The method of claim 1, wherein the at least one oligosaccharide is found in a ratio of 1800:1 (w/w) of CBD.

5. The method of claim 1, wherein the at least one oligosaccharide is found in a ratio of 2000:1 (w/w) of CBD.

6. The method of claim 1, wherein the at least one oligosaccharide is found in a ratio of 2200:1 (w/w) of CBD.

7. The method of claim 1, wherein the mixing of the oligosaccharide CBD slurry in the pressurized chamber occurs at temperature in the range between about 175° F. to 225° F.

8. The method of claim 1, wherein the at least one oligosaccharide comprises at least a fructooligosaccharide, a galactooligosaccharide, or a combination thereof.

9. The method of claim 1, wherein the evaporation vessel within the heating chamber is heated to a temperature in the range between about 225° F. to 300° F.

10. The method of claim 1, wherein the colloidal mixture is distributed into the tray forming the distributed mixture layer with a depth in the range between about 2.0 inches and 4.0 inches.

11. An oligosaccharide encapsulated cannabidiol formulation comprising:
   cannabidiol (CBD); and
   at least one oligosaccharide, the at least one oligosaccharide present in a ratio ranging between about 1000:1 to 2200:1 (w/w) of CBD.

12. The oligosaccharide encapsulated cannabidiol formulation of claim 11, wherein the at least one oligosaccharide comprises fructooligosaccharide.

13. The oligosaccharide encapsulated cannabidiol formulation of claim 11, wherein the at least one oligosaccharide comprises galactooligosaccharide.

14. The oligosaccharide encapsulated cannabidiol formulation of claim 11, wherein the at least one oligosaccharide is found in a ratio in the range between about 1800:1 to 2200:1 (w/w) of CBD.

15. The oligosaccharide encapsulated cannabidiol formulation of claim 11, wherein the at least one oligosaccharide is found in a ratio in the range between about 2000:1 to 2200:1 (w/w) of CBD.

16. The oligosaccharide encapsulated cannabidiol formulation of claim 11, wherein the at least one oligosaccharide is found in a ratio of about 1800:1 (w/w) of CBD.

17. The oligosaccharide encapsulated cannabidiol formulation of claim 11, wherein the at least one oligosaccharide is found in a ratio of 2000:1 (w/w) of CBD.

18. The oligosaccharide encapsulated cannabidiol formulation of claim 11, wherein the at least one oligosaccharide is found in a ratio of 2200:1 (w/w) of CBD.

* * * * *